United States Patent
Jeon et al.

(10) Patent No.: US 9,434,682 B2
(45) Date of Patent: Sep. 6, 2016

(54) REACTIVE MESOGEN COMPOUND HAVING SUPERIOR THERMOSTABILITY AND HIGH BIREFRINGENCE AND METHOD OF PREPARING THE SAME

(71) Applicant: AEKYUNG CHEMICAL CO., LTD., Seoul (KR)

(72) Inventors: Yoon-Tae Jeon, Daejeon (KR); Do-Yeon Kim, Daejeon (KR); Yun-Sun Do, Hwaseong-si (KR); Gi-Woo Lee, Daejeon (KR); Hueong-Nam Park, Daejeon (KR); Kwang-Sik Choi, Daejeon (KR)

(73) Assignee: Aekyung Chemical Co., Ltd. (KR)

( * ) Notice: Subject to any disclaimer, the term of this patent is extended or adjusted under 35 U.S.C. 154(b) by 0 days.

(21) Appl. No.: 14/805,715

(22) Filed: Jul. 22, 2015

(65) Prior Publication Data

US 2015/0361033 A1  Dec. 17, 2015

Related U.S. Application Data

(63) Continuation of application No. PCT/KR2013/000679, filed on Jan. 28, 2013.

(30) Foreign Application Priority Data

Jan. 23, 2013 (KR) .................. 10-2013-0007368

(51) Int. Cl.

| C07C 69/00 | (2006.01) |
| C07C 249/02 | (2006.01) |
| C07C 219/14 | (2006.01) |
| C09K 19/38 | (2006.01) |
| C09K 19/06 | (2006.01) |
| C09K 19/20 | (2006.01) |
| C09K 19/22 | (2006.01) |
| C07C 65/00 | (2006.01) |
| C07C 45/64 | (2006.01) |
| C07C 51/367 | (2006.01) |
| C07C 67/40 | (2006.01) |
| C07D 309/12 | (2006.01) |
| C09K 19/04 | (2006.01) |

(52) U.S. Cl.
CPC ............. C07C 249/02 (2013.01); C07C 45/64 (2013.01); C07C 51/367 (2013.01); C07C 65/00 (2013.01); C07C 67/40 (2013.01); C07C 219/14 (2013.01); C07D 309/12 (2013.01); C09K 19/062 (2013.01); C09K 19/2014 (2013.01); C09K 19/22 (2013.01); C09K 19/38 (2013.01); C09K 2019/0448 (2013.01)

(58) Field of Classification Search
CPC . C07C 51/367; C07C 219/14; C07C 249/02; C07C 45/64; C07C 65/00; C07C 65/21; C07C 67/40; C07C 309/12; C09K 19/062; C09K 19/2014; C09K 19/22; C09K 19/38; C09K 2019/0448

See application file for complete search history.

(56) References Cited

U.S. PATENT DOCUMENTS

| 2013/0109825 A1* | 5/2013 | Mizumura | ................. C08J 5/18 |
| | | | 526/292.2 |
| 2013/0123453 A1* | 5/2013 | Mizumura | ............ C07C 251/24 |
| | | | 526/292.2 |

FOREIGN PATENT DOCUMENTS

| JP | 002012006843 | * | 1/2012 |
| JP | 002012006997 | * | 1/2012 |

OTHER PUBLICATIONS

Written opinion for KR2013000679, 2013.*

* cited by examiner

*Primary Examiner* — Yevegeny Valenrod
*Assistant Examiner* — Blaine G Doletski
(74) *Attorney, Agent, or Firm* — Park & Associates IP Law, P. C.

(57) ABSTRACT

Disclosed are a novel reactive mesogen compound having superior thermostability, high birefringence and a simple preparation process while possessing unique liquid crystal characteristics having molecular orientation by forming a polymer network through photopolymerization, and a method of preparing the same. The novel reactive mesogen compound according to the present invention is represented by Formula 3 below.

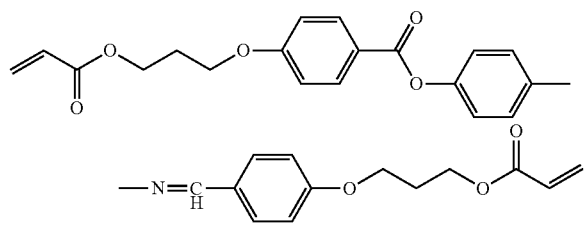

Formula 3

3 Claims, 4 Drawing Sheets

FIG. 4

REACTIVE MESOGEN COMPOUND HAVING SUPERIOR THERMOSTABILITY AND HIGH BIREFRINGENCE AND METHOD OF PREPARING THE SAME

REFERENCE TO RELATED APPLICATIONS

This is a continuation of pending International Patent Application PCT/KR2013/000679 filed on Jan. 28, 2013, which designates the United States and claims priority of Korean Patent Application No. 10-2013-0007368 filed on Jan. 23, 2013, the entire contents of which are incorporated herein by reference.

FIELD OF THE INVENTION

The present invention relates to a novel reactive mesogen compound and a method of preparing the same. More particularly, the present invention relates to a novel reactive mesogen compound having superior thermostability, high birefringence and a simple preparation process while possessing unique liquid crystal characteristics such as molecular orientation by forming a polymer network through photopolymerization, and a method of preparing the same.

BACKGROUND OF THE INVENTION

As digitalization and informatization are accelerated, a lot of IT is used in daily life and much development in display technology of IT equipment is underway. As representative examples of a flat-panel display, there are LCDs, PDPs, OLEDs, etc. Thereamong, LCDs are most common.

Since an LCD in which liquid crystal and semiconductor technology are combined has advantages such as light weight and low consumption power, it is currently, broadly used in large TVs, PC monitors, display devices of various measurement equipment, PMP or MP3 equipment, navigators of vehicles, cellular phones, etc.

In order to realize large high-quality LCDs, a wide viewing angle, high brightness, a high contrast ratio, a fast response rate, etc. are required. As broadly used modes among currently known LCD operation modes, there are twisted nematic (TN), super twisted nematic (STN), vertical alignment (VA) and in-plane switching (IPS).

Stick-type liquid crystal molecules used in such LCDs are orientated in a given direction on a polymer alignment layer. Such orientation causes change in apparent Δnd of liquid crystal according to a viewing angle in each LCD, thus limiting wide viewing angles in LCDs.

When liquid crystal molecule arrangement is changed by application of an electric field, proceeding light meets with liquid crystal molecule at different angles, and thus, a polarization state of transmitted light varies. As a result, when transmitted light passes through a polarization plate of an LCD surface, some light is leaked. In this case, luminance between a front side and an inclined angle is different or contrast reversal occurs.

Various attemps have been made to overcome such phenomena and secure a wide viewing angle. Thereamong, a method using a compensation film is currently, relatively broadly used. A compensation film has a changed value in a phase difference according to increase of a viewing angle and performs compensation using an opposite direction film.

To correspond to various LCD modes, a variety of compensation films are required. Currently, compensation film technology uses a thick oriented film and, is limited to liquid crystal films. When, as a material of such a compensation film, reactive liquid crystal is used, a highly efficient compensation film may be realized. In order to realize a highly-efficient ultra-thin compensation film, there is an urgent need for reactive liquid crystal compounds having unique liquid crystal characteristics such as molecular orientation by forming a polymer network through photopolymerization, and superior thermostability and a simple preparation process. However, currently, commercially available reactive liquid crystal compounds have a complex preparation process in order to express unique liquid crystal characteristics and low thermostability.

As a conventional reactive liquid crystal compound, Korean Patent No. 10-1006145 discloses a discoid liquid crystal compound, represented by a formula given below, having various-size alkyl, polyethylene glycol, phenyl alkyl ester and phenyl polyethylene glycol ester chains as side chains from the center of triphenylene for temperature range control of a liquid crystal phase, and phenylacryloyl (cinnamoyl), naphthyl acryloyl and biphenyl acryloyl at side chain terminals for photocrosslinking at various wavelengths.

In addition, Korean Application Pub. No. 10-1069555 discloses a rod-type liquid crystal compound in which (1) phenyl or an acetylene functional group for providing high birefringence, (2) various-length alkyl as side chains for controlling a temperature range of a liquid crystal phase, and (3) acryloyl, methacryloyl, phenylacryloyl (cinnamoyl) or furylacryloyl as a terminal group for photocrosslinking reaction are introduced into the center of hydroquinone substituted with a high-birefringence mesogen compound containing a photoreactive group wherein a film may be formed through photocrosslinking reaction by ultraviolet (UV) irradiation.

In addition, Korean Application Pub. No. 10-2011-0104416 discloses a reactive mesogen compound represented by Formula P1-A1-(Z1-A2)n-P2 (wherein P1 and P2 are each independently selected from the group consisting of acrylate, methacrylate, vinyl, vinyloxy and epoxy, A1 and A2 are each independently selected from the group consisting of 1,4-phenylene and naphthalene-2,6-diyl, Z1 is one of COO—, OCO— and a single bond, and n is one of 0, 1 and 2.

Furthermore, Korean Application Pub. No. 10-2011-0112372 discloses a mesogen compound represented by formulas below.

IIA

However, conventional reactive mesogen compounds have problems such as a complex synthesis process, a low birefringence and low thermostability.

In particular, in order to satisfy requirements of a variety of compensation films in lcd displays, two types such as an oriented film and an orientation-coated reactive liquid crystal are used.

As a material of a compensation film orientation-coated with a reactive liquid crystal, a reactive liquid crystal having a high birefringence is required. In order to realize an ultra-thin compensation film, a reactive liquid crystal compound having a high birefringence is essential.

However, currently available reactive liquid crystal compounds for a compensation film have a low birefringence of less than 1.6.

Accordingly, the present inventors discovered a novel reactive mesogen compound having a simple synthesis process, superior thermostability and high birefringence, and a method of preparing the same, thus completing the present invention.

SUMMARY OF THE INVENTION

Therefore, the present invention has been made in view of the above problems, and it is an object of the present invention to provide a novel reactive mesogen compound and a method of preparing the same. More particularly, the present invention relates to a novel reactive mesogen compound having superior thermostability, high birefringence and a simple preparation process while possessing unique liquid crystal characteristics such as molecular orientation by forming a polymer network through photopolymerization, and a method of preparing the same.

In accordance with an aspect of the present invention, the above and other objects can be accomplished by the provision of a novel reactive mesogen compound represented by Formula 1 below.

Formula 1 wherein $P_1$ and $P_2$ are each independently selected from $CH_2=CH_2—$, $HC≡C—$, $CH_2=CH—CH_2—$, $W^1HCOCH—$, $CH_2=CW^1—COO—$, $CH_2=CW^2—(O)_{k1}—$, $CH_3—CH=CH—O—$, $HO—CW^2W^3—$, $HS—CW^2W^3—$, $HW^2N—$, $HO—CW^2W^3—NH—$, $CH_2=CW^1—CO—NH—$, $CH_2=CH—(COO)_{k1}$-Phe-$(O)_{k2}—$, Phe-CH=CH—, HOOC—, NCO—, OCN—, SCN—, $W^4W^5W^6Si—$, wherein $W^1$ is H, Cl, CN, phenyl or $C_1$ to $C_5$ alkyl, $W^2$ and $W^3$ are each independently hydrogen or $C_1$ to $C_5$ alkyl, $W^4$, $W^5$, and $W^6$ are each independently Cl, $C_1$ to $C_5$ oxycarbonyl alkyl or oxy alkyl, Phe is 1,4-phenylene, and k1 and k2 are each independently 0 or 1, $Sp_1$ and $Sp_2$ are spacer groups and are each independently 1 to 25 carbon atoms, $X_1$ and $X_2$ are each independently —O—, —S—S—CO—, —CO—S—, —CO—, —COO—, —OCO—, —O—COO—, —CO—NR—, —NR—CO——NR—CO—NR—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF=CF—, —CF$_2$CF$_2$—, —CH=N—, —N=CH—, —N=N—, —CH=CR—, —CX=CX—, —C≡C—, —CH=CH—COO—, —OCO—CH=CH—, —OCO—CH=CH—, —NH—, —N=CH—S—, —CH=N—S—, —SO$_2$—, —O—Si(OH)$_2$—O— or a single bond, $n_1$ and $n_2$ are each independently 0 or 1, $Z_1$ and $Z_2$ are each independently —O—, —S—, —S—CO—, —CO—S—, —CO—, —COO—, —OCO—, —O—COO—, —CO—NR—, —NR—CO—, —NR—CO—NR—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF=CF—, —CF$_2$CF$_2$—, —CH=N—, —N=CH—, —N=N—, —CH=CR—, —CX=CX—, —C≡C—, —CH=CH—COO—, —OCO—CH=CH—, —NH—, —N=CH—S—, —CH=N—S—, —SO$_2$—, —O—Si(OH)$_2$—O— or a single bond, $A_1$ and $A_2$ are each independently phenyl, 1,4-phenylene, 1,4-cyclohexenylene or naphthalene, and may be singly substituted or multiply substituted with F, Cl, CN, OH, NO$_2$, or $C_1$ to $C_7$ alkyl, alkoxy or alkanoyl, $m_1$ or $m_2$ are each independently 0, 1 or 2 ($mn_1+m_2<3$), $L_1$ and $L_2$ are each independently F, Cl, CN, OH, NO$_2$ or $C_1$ to $C_7$ alkyl, alkoxy or alkanoyl, (wherein H of one or more carbon chains may be substituted with F or Cl.), and r is 0, 1, 2, 3 or 4.

In addition, the novel reactive mesogen compound represented by Formula 1 may be the novel reactive mesogen compound represented by Formula 2 below.

$X_1$ and $X_2$ are each independently —O—, —S—, —S—CO—, —CO—S—, —CO—, —COO—, —OCO—, —O—COO—, —CO—NR—, —NR—CO—, —NR—CO—NR—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF=CF—, —CF$_2$CF$_2$—, —CH=N—, —N=CH—, —N=N—, —CH=CR—, —CX=CX—, —C≡C—, —CH=CH—COO—, —OCO—CH=CH—, —NH—, —N=CH—S—, —CH=N—S—, —CH—S—, —SO$_2$—, —O—Si(OH)$_2$—O— or a single bond, $n_1$ and $n_2$ are each independently 0 or 1, $Z_2$ is —O—, —S—, —S—CO—, —CO—S—CO—, —COO—, —OCO—, —O—COO—, —CO—NR—, —NR—CO—, —NR—CO—NR—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF=CF—, —CF$_2$CF$_2$—, —CH=N—, —N=CH—, —N=N—, —CH=CR—, —CX=CX—, —C≡O—, —CH=CH—COO—, —OCO—CH=CH—, —NH—, —N=CH—S—, —CH=N—S—, —SO$_2$—, —O—Si(OH)$_2$—O— or a single bond, Formula 2 wherein $P_1$ and $P_2$ are each independently selected from CH$_2$=CH$_2$—, HC≡C—, CH$_2$=CH—CH$_2$—, W$^1$HCOCH—, CH$_2$=CW$^1$—COO—, CH$_2$=CW$^2$—(O)$_{k1}$—, CH$_3$—CH=CH—O—, HO—CW$^2$W$^3$—, HS—CW$^2$W$^3$—, HW$^2$N—, HO—CW$^2$W$^3$—NH—, CH$_2$=CW$^1$—CO—NH—, CH$_2$=CH—(COO)$_{k1}$-Phe-(O)$_{k2}$—, Phe-CH=CH—, HOOC—, NCO—, OCN—, SCN—, W$^4$W$^5$W$^6$Si—,

$A_2$ is phenyl, 1,4-phenylene, 1,4-cyclohexenylene or naphthalene, and may be singly substituted or multiply substituted with F, Cl, ON, OH, NO$_2$, or $C_1$ to $C_7$ alkyl, alkoxy, alkanoyl, and $m_2$ is 0, 1 or 2.

In addition, the novel reactive mesogen compound represented by Formula 1 may be a novel reactive mesogen compound represented by Formula 3 below.

Formula 3

, and , wherein W$^1$ is H, Cl, CN, phenyl or $C_1$ to $C_5$ alkyl, W$^2$ and W$^3$ are each independently hydrogen or $C_1$ to $C_5$ alkyl, W$^4$, W$^5$, and W$^6$ are each independently Cl, $C_1$ to $C_5$ oxycarbonyl alkyl or oxy alkyl, Phe is 1,4-phenylen, and k1 and k2 are each independently 0 or 1,

$Sp_1$ and $Sp_2$ are spacer groups and are each independently 1 to 25 carbon atoms,

In accordance with another aspect of the present invention, there is provided a method of preparing the novel reactive mesogen compound of Formula 3, the method including preparing a compound of Formula 4 below; preparing a compound of Formula 5 below from the compound of Formula 4 below; preparing a compound of Formula 6 below; preparing a compound of Formula 7 below from the compound of Formula 6 below; preparing a compound of Formula 8 below from the compound of Formula 7 below; preparing a compound of Formula 9 below by reacting the compound of Formula 5 below and a compound of Formula 8 below; preparing a compound of Formula 10 below from the compound of Formula 9 below; and preparing the compound of Formula 3 from the compound of Formula 10 below.

Formula 4

Formula 5

Formula 6

Formula 7

Formula 8

Formula 9

Formula 10

In accordance with another aspect of the present invention, there is provided

In addition, the compound of Formula 5 may be prepared by reacting through dropping an acryloyl chloride solution diluted in tetrahydrofuran (THF) into a mix solution of the compound of Formula 4, triethylamine (TEA) and methylene chloride (MC).

The compound of Formula 8 may be prepared by reacting at 100° C. while stirring a mix solution of the compound of Formula 7, aminophenol (4-aminophenol), dimethylacetamide (DMAC) and ethylacetate (EAc).

As described above, a novel reactive mesogen compound according to the present invention has unique liquid crystal characteristics such as molecular orientation by forming a polymer network through photopolymerization, superior thermostability, and a simple preparation process. Accordingly, the novel reactive mesogen compound as an important material of a wide-viewing-angle liquid crystal display device of large-scale screens may be prepared into a compensation film and phase difference film and realizes an efficient thin-thickness compensation film and phase difference film, and thus, may be effectively used in liquid crystal display devices.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Now, the present invention will be described in more detail with reference to the accompanying drawings. These examples are provided for illustrative purposes only and should not be construed as limiting the scope and spirit of the present invention.

The present invention is characterized by a novel reactive mesogen compound represented by Formula 1 below.

Formula 1 wherein, $P_1$ and $P_2$ are each independently selected from $CH_2=CH_2-$, $HC\equiv C-$, $CH_2=CH-CH_2-$, $W^1HCOCH-$, $CH_2=CW^1-COO-$, $CH_2=CW^2-(O)_{k1}-$, $CH_3-CH=CH-O-$, $HO-CW^2W^3-$, $HS-CW^2W^3-$, $HW^2N-$, $HO-CW^2W^3-NH-$, $CH_2=CW^1-CO-NH-$, $CH_2=CH-(COO)_{k1}-Phe-$ $(O)_{k2}$—, Phe-CH=CH—, HOOC—, NCO—, OCN—, SCN—, $W^4W^5W^6Si$—, and wherein $W^1$ is H, Cl, CN, phenyl or $C_1$ to $C_5$ alkyl, $W^2$ and $W^3$ are each independently hydrogen or $C_1$ to $C_5$ alkyl, $W^4$, $W^5$, and $W^6$ are each independently Cl, $C_1$ to $C_5$ oxycarbonyl alkyl or oxy alkyl, Phe is 1,4-phenylene k1 and k2 are each independently 0 or 1, $Sp_1$, and $Sp_2$ are spacer groups and are each independently 1 to 25 carbon atoms, $X_1$ and $X_2$ are each independently —O—, —S—, —S—CO—, —CO—S—, —CO—, —COO—, —OCO—, —O—COO—, —CO—NR—, —NR—CO—, —NR—CO—NR—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF=CF—, —CF$_2$CF$_2$—, —CH=N—, —N=CH—, —N=N—, —CH=CR—, —CX=CX—, —C≡C—, —CH=CH—COO—, —OCO—CH=CH—, —NH—, —N=CH—S—, —CH=N—S—, —SO$_2$—, —O—Si(OH)$_2$—O— or a single bond, $n_1$ and $n_2$ are each independently 0 or 1, $Z_1$ and $Z_2$ are each independently —O—, —S—, —S—CO—, —CO—S—, —CO—, —COO—, —OCO—, —O—COO—, —CO—NR—, —NR—CO—, —NR—CO—NR—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF=CF—, —CF$_2$CF$_2$—, —CH=N—, —N=CH—, —N=N—, —CH=CR—, —CX=CX—, —C≡C—, —CH=CH—COO—, —OCO—CH=CH—, —NH—, —N=CH—S—, —CH=N—S—, —SO$_2$—, —O—Si(OH)$_2$—O— or a single bond, $A_1$ and $A_2$ are each independently phenyl, 1,4-phenylene, 1,4-cyclohexenylene or naphthalene, and may be singly substituted or multiply substituted with F, Cl, CN, OH, NO$_2$, or $C_1$ to $C_7$ alkyl, alkoxy or alkanoyl,

$m_1$ or $m_2$ are each independently 0, 1 or 2 ($m_1+m_2<3$), $L_1$ and $L_2$ are each independently F, Cl, CN, OH, NO$_2$ or $C_1$ to $C_7$ alkyl, alkoxy or alkanoyl, (wherein H of one or more carbon chains may be substituted with F or Cl.) and r is 0, 1, 2, 3 or 4.

In addition, the novel reactive mesogen compound represented by Formula 1 is a novel reactive mesogen compound represented by Formula 2 below.

wherein $P_1$ and $P_2$ are each independently selected from CH$_2$=CH$_2$—, HC≡C—, CH$_2$=CH—CH$_2$—, $W^1$HCOCH—, CH$_2$=CW$^1$—COO—, CH$_2$=CW$^2$—(O)$_{k1}$—, CH$_3$—CH=CH—O—, HO—CW$^2$W$^3$—, HS—CW$^2$W$^3$—, HW$^2$N—, HO—CW$^2$W$^3$—NH—, CH$_2$=CW$^1$—CO—NH—, CH$_2$=CH—(COO)$_{k1}$-Phe-(O)$_{k2}$—, Phe-CH=CH—, HOOC—, NCO—, OCN—, SCN—, $W^4W^5W^6Si$—, and wherein $W^1$ is H, Cl, CN, phenyl or $C_1$ to $C_5$ alkyl, $W^2$ and $W^3$ are each independently hydrogen or $C_1$ to $C_5$ alkyl, $W^4$, $W^5$, and $W^6$ are each independently Cl, $C_1$ to $C_5$ oxycarbonyl alkyl or oxy alkyl, Phe is 1,4-phenylene, and k1 and k2 are each independently 0 or 1, $Sp_1$ and $Sp_2$ are spacer groups and are each independently 1 to 25 carbon atoms, $X_1$ and $X_2$ are each independently —O—, —S—, —S—CO—, —CO—S—, —CO—, —COO—, —OCO—, —O—COO—, —CO—NR—, —NR—CO—, —NR—CO—NR—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF=CF—, —CF$_2$CF$_2$—, —CH=N—, —N=CH—, —N=N—, —CH=CR—, —CX=CX—, —C≡O—, —CH=CH—COO—, —OCO—CH=CH—, —NH—, —N=CH—S—, —CH=N—S—, —SO$_2$—, —O—Si(OH)$_2$—O— or a single bond, $n_1$ and $n_2$ are each independently 0 or 1,

$Z_2$ is —O—, —S—, —S—CO—, —CO—S—, —CO—, —COO—, —OCO—, —O—COO—, —CO—NR—, —NR—CO—, —NR—CO—NR—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF=CF—, —CF$_2$CF$_2$—, —CH=N—, —N=CH—, —N=N—, —CH=CR—, —CX=CX—, —C≡C—, —CH=CH—COO—, —OCO—CH=CH—, —NH—, —N=CH—S—, —CH=N—S—, —SO$_2$—, —O—Si(OH)$_2$—O— or a single bond,

$A_2$ is phenyl, 1,4-phenylene, 1,4-cyclohexenylene or naphthalene, and may be singly substituted or multiply substituted with F, Cl, ON, OH, NO$_2$, or $C_1$ to $C_7$ alkyl, alkoxy or alkanoyl, and $m_2$ is 0, 1 or 2.

In addition, the novel reactive mesogen compound represented by Formula 1 is a novel reactive mesogen compound represented by Formula 3 below.

Formula 2

Formula 3

In addition, a method of preparing the novel reactive mesogen compound of Formula 3 includes preparing a compound of Formula 4 below; preparing a compound of Formula 5 below from the compound of Formula 4 below; preparing a compound of Formula 6 below; preparing a compound of Formula 7 below from the compound of Formula 6 below; preparing a compound of Formula 8 below from the compound of Formula 7 below; preparing a compound of Formula 9 below by reacting the compound of Formula 5 below and a compound of Formula 8 below; preparing a compound of Formula 10 below from the compound of Formula 9 below; and preparing the compound of Formula 3 from the compound of Formula 10 below.

Formula 4

Formula 5

Formula 6

Formula 7

Formula 8

Formula 9

Formula 10

In addition, the compound of Formula 5 is prepared by reacting through dropping an acryloyl chloride solution diluted in tetrahydrofuran (THF) into a mix solution of the compound of Formula 4, triethylamine (TEA) and methylene chloride (MC).

In addition, the compound of Formula 8 is prepared by reacting at 100° C. while stirring a mix solution of the compound of Formula 7, aminophenol (4-aminophenol), dimethylacetamide (DMAC) and ethylacetate (EAc).

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

EXAMPLE 1

Synthesis of Compound According to Formula 4

An aqueous solution of NaOH (1 mol) and KI (0.05 mmol) was added to a solution of 4-hydroxybenzoic acid (0.5 mmol) and 400 mL EtOH solution under a nitrogen atmosphere and stirred. After stirring for 30 minutes, an EtOH solution including bromopropanol (0.55 mmol) was dropped thereinto, and then, reacted for 24 hours after elevating to 80° C. A solvent was removed from a reaction product and hydrochloric acid-treatment was carried out. A solid phase was isolated through filteration, and 4-(3-hydroxypropoxy)benzoic acid as a compound of Formula 4 was synthesized.

EXAMPLE 2

Synthesis of Compound According to Formula 5

At 0° C. or less, a solution of acryloil chloride (0.6 mmol) diluted in THF was dropped into a solution of 4-(3-hydroxypropanoxy) benzoic acid (0.5 mmol) as the compound of Formula 4 synthesized according to Example 1, TEA (1.1 mol) and MC 500 mL and reacted for 10 hours. A solvent was removed from a reaction product and extraction was carried out using distilled water. Subsequently, column separation was carried out using an EAc/Hexane eluent, and 4-(3-(acryloyloxy)propoxy)benzoic acid as a compound of Formula 5 was synthesized.

EXAMPLE 3

Synthesis of Compound According to Formula 6

Under a nitrogen atmosphere, an aqueous $K_2CO_3$ (1 mol) solution was added to a solution of 4-hydroxybenzaldehyde (0.55 mmol) and 200 mL of acetone, and stirred. After stirring for 30 minutes, an acetone solution including bromopropanol (0.5 mmol) was dropped thereto, and then reacted for 12 hours after elevating to 50° C. A solvent was removed from a reaction product and extraction was carried out using EAc and distilled water. A reaction product obtained from an organic layer was separated through a silica column using a Hexane/EAc eluent, and 4-(3-hydroxypropoxy)benzaldehyde as a compound of Formula 6 was synthesized.

EXAMPLE 4

Synthesis of Compound According to Formula 7

4-(3-hydroxypropoxy)benzaldehyde (0.5 mmol) as the compound of Formula 6 synthesized according to Example 3, pyridinium p-toluenesulfonate (0.05 mmol) and 200 ml of MC were mixed under a nitrogen atmosphere. After diluting 3,4-dihydropyran (0.55 mmol) in $CH_2Cl_2$ and then dropping into the mixture, reaction was carried out at room temperature for six hours. Extraction was carried out using distilled water and MC, a reaction product obtained from an organic layer was separated through a silica column using a Hexane/EAc eluent, and 4-(3-(tetrahydro-2H-pyran-2-yloxy)propoxy)benzaldehyde as a compound of Formula 7 was synthesized.

EXAMPLE 5

Synthesis of Compound According to Formula 8

4-(3-(tetrahydro-2H-pyran-2-yloxy)propoxy)benzaldehyde (0.55 mmol) as the compound of Formula 7 synthesized according to Example 4, 4-aminophenol (0.5 mmol), 50 ml of DMAC and 50 ml of EAc were stirred under a nitrogen atmosphere. Temperature was elevated to 100° C. and reacted for 24 hours. A solvent was removed from the reaction product, and extraction was carried out using distilled water and EAc. Subsequently, a reaction product obtained from an organic layer was separated through a silica column using a Hexane/EAc eluent, and 4-(4-(3-(tetrahydro-2H-pyran-2-yloxy)propoxy)benzylideneamino)phenol as the compound of Formula 8 was synthesized.

EXAMPLE 6

Synthesis of Compound According to Formula 9

4-(3-(acryloyloxy)propoxy)benzoic acid (1.1 mol) as the compound of Formula 5 synthesized according to Example 2, DCC (1.1 mmol) and DMAP (0.11 mmol) were dissolved in an MC solution and stirred. Thereinto, 4-(4-(3-(tetrahydro-2H-pyran-2-yloxy)propoxy)benzylideneamino)phenol (1.0 mmol), dissolved in an MC solution, as the compound of Formula 8 synthesized according to Example 5, was added dropwise and reacted for eight hours. Extraction was carried out using distilled water and MC. Subsequently, a reaction product obtained from an organic layer was separated through a silica column using a Hexane/EAc eluent, and 4-(4-(3-(tetrahydro-2H-pyran-2-yloxy)propoxy)benzylideneamino)phenyl 4-(3-(acryloyloxy)propoxy)benzoate as a compound of Formula 9 was synthesized.

EXAMPLE 7

Synthesis of Compound According to Formula 10

4-(4-(3-(tetrahydro-2H-pyran-2-yloxy)propoxy)benzylideneamino)phenyl 4-(3-(acryloyloxy)propoxy)benzoate (1 mmol) as the compound of Formula 9 synthesized according to Example 6 was dissolved in 100 ml of MeOH and stirred at room temperature. 10 ml of 10% aqueous HCl solution was added dropwise thereinto and then reacted for one hour. A solvent was removed, and extraction was carried out using distilled water and MC. Subsequently, a reaction product obtained from an organic layer was separated through a silica column using a Hexane/EAc eluent, and 4-(4-(3-hydroxypropoxy)benzylideneamino)phenyl 4-(3-(acryloyloxy)propoxy)benzoate as a compound of Formula 10 was synthesized.

EXAMPLE 8

Synthesis of Compound According to Formula 3

At 0° C. or less, an acryloyl chloride (0.6 mmol) solution diluted in THF was added dropwise to a solution of 4-(4-(3-hydroxypropoxy)benzylideneamino)phenyl 4-(3-(acryloyloxy)propoxy)benzoate(0.5 mmol) as the compound of Formula 10 synthesized according to Example 7, TEA (1.1 mol) and 500 mL of an MC solution, and was reacted for 10 hours. A solvent was removed from a reaction product and by extracting with MC. Subsequently, column separation was carried out using an EAc/Hexane eluent, and a 4-(4-(3-(acryloyloxy)propoxy)benzylideneamino)phenyl 4-(3-(acryloyloxy)propoxy)benzoate target material as a compound of Formula 3 was synthesized. A synthesis process of the compound of Formula 3 is as follows.

[Formula 3]

Figure 1:
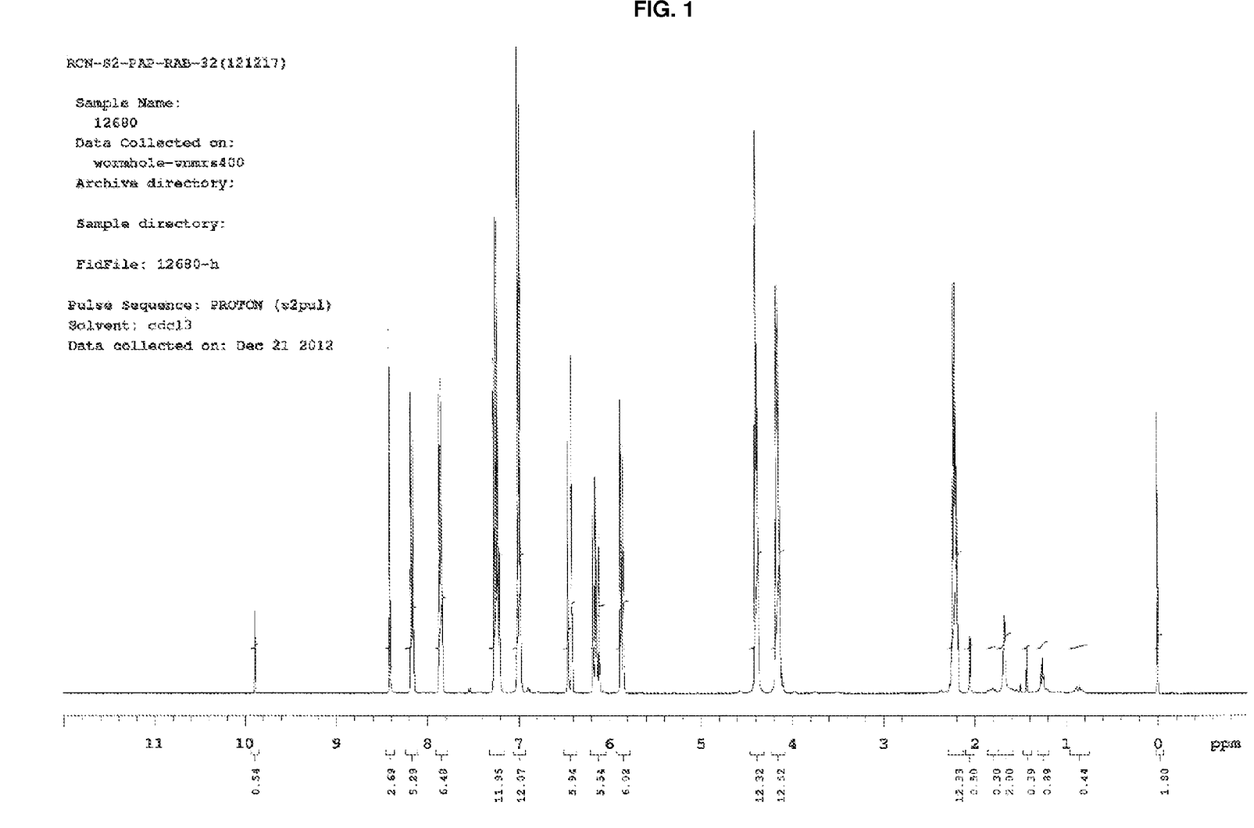
FIG. 1 illustrates a $^1$H-NMR graph of a compound of Formula 3 according to the present invention.
Figure 2:
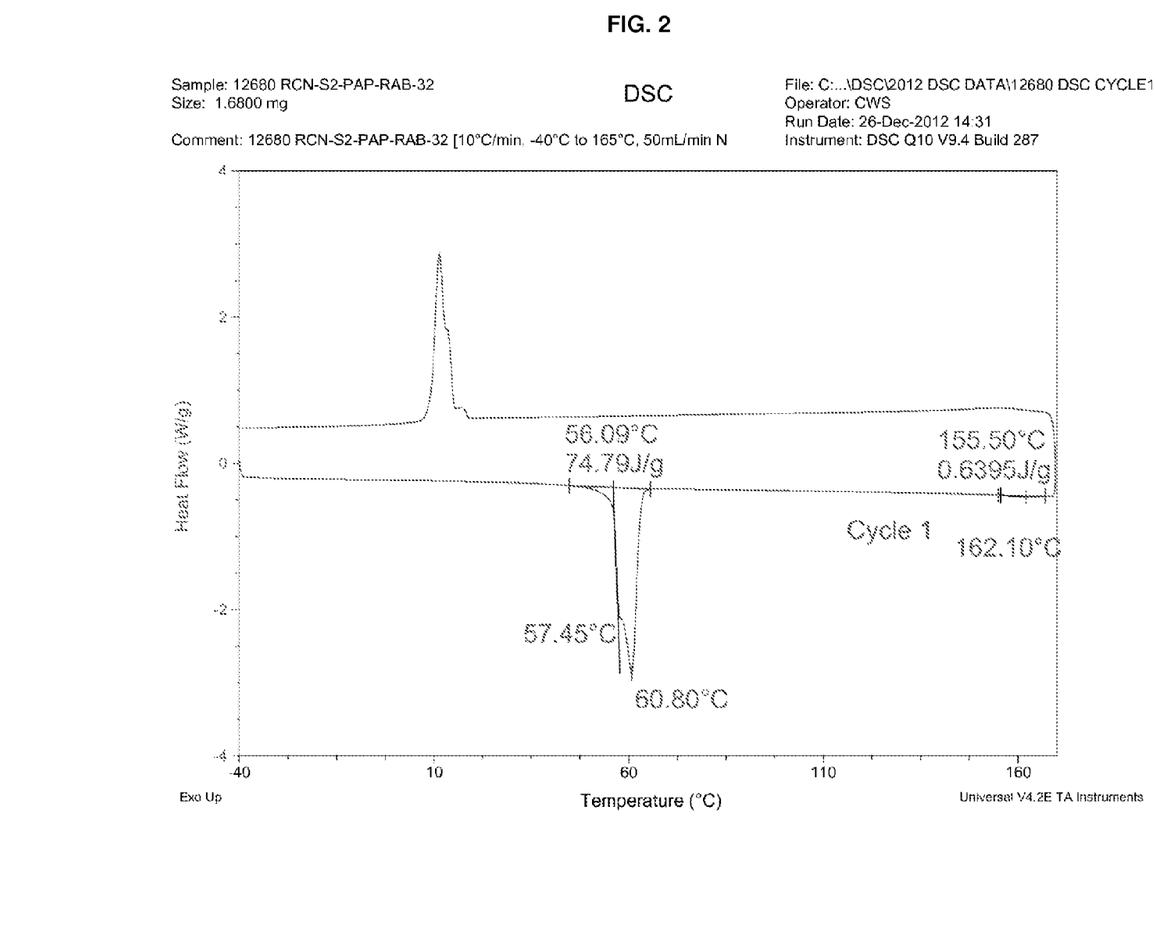
FIG. 2 illustrates a DSC graph of a compound of Formula 3 according to the present invention.
Figure 3:
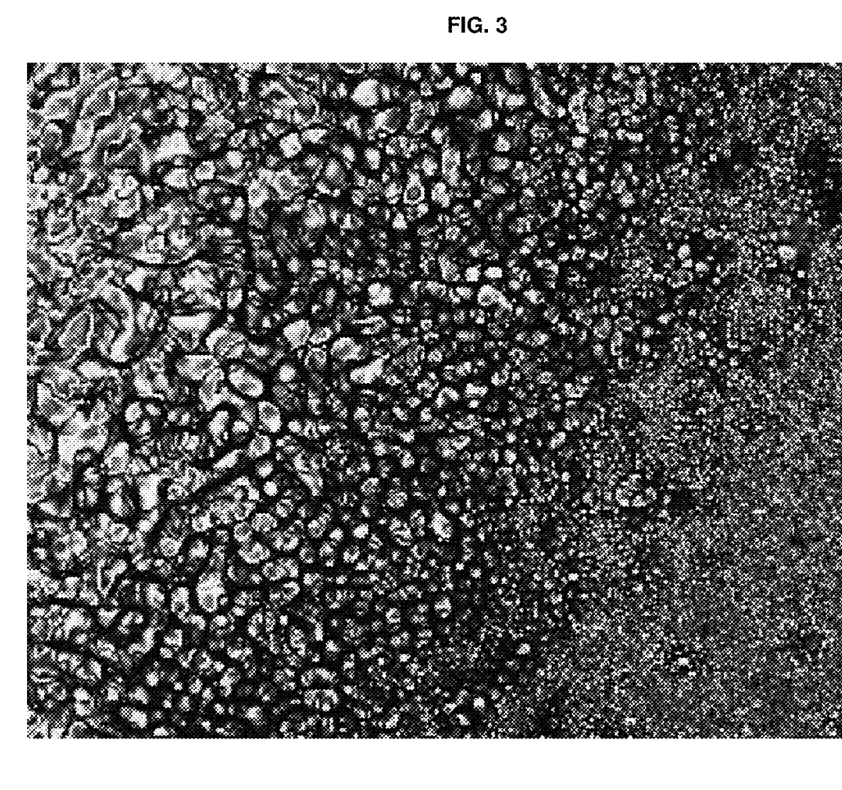
FIG. 3 illustrates a nematic phase photograph, observed with a polarization microscope, of a compound of Formula 3 according to the present invention.
Figure 4:
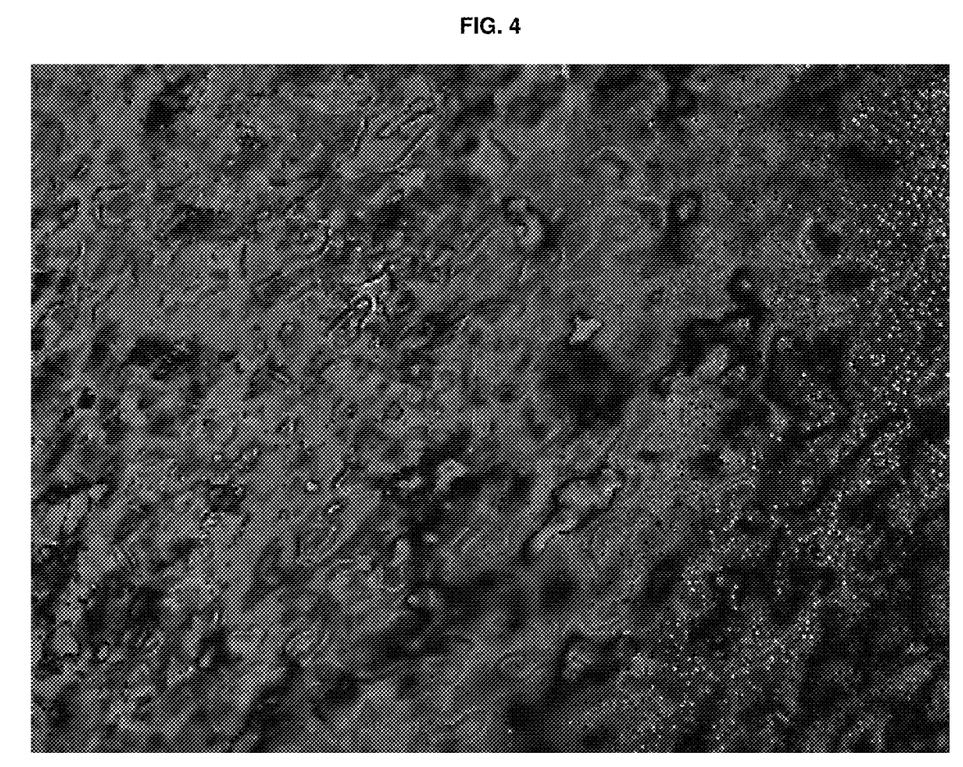
FIG. 4 illustrates a crystalline phase-nematic phase photograph, observed with a polarization microscope, of a compound of Formula 3 according to the present invention.

Regarding the compound of Formula 3, a 1H-NMR graph is illustrated in FIG. 1, a DSC graph was illustrated in FIG. 2, a polarization microscope crystalline phase photograph is illustrated in FIG. 3, and a crystalline phase-nematic phase photograph is illustrated in FIG. 4.

As illustrated in FIG. 2, the compound of Formula 3 according to the present invention represents a nematic phase, as illustrated in FIG. 3 and FIG. 4, within a broad temperature range of 56° C. to 160° C. Accordingly, it can be confirmed that the compound according to the present invention has unique liquid crystal characteristics such as molecular orientation and superior thermostability.

EXAMPLE 9

Birefringence Measurement of Compound According to Formula 3

Using an ABBE refractometer, DR-M4 from ATAGO Corporation, a horizontal—direction ($n_e$) refractive index and a vertical-direction ($n_o$) refractive index of an orientated liquid crystal molecule of the compound of Formula 3 were measured. Birefringence difference ($\Delta n$) between the horizontal-direction refractive index ($n_e$) and the vertical-direction refractive index ($n_o$) was measured and results are summarized in Table 1 below.

EXAMPLE 10

Temperature Measurement of Liquid Crystal Phase of Formula 3

Using a differential scanning calorimeter (DSC), the temperature of liquid crystal phase of the compound according to Formula 3 was measured. The measurement was carried out under conditions of 10° C./min, temperature range of 40° C. to 165° C. and nitrogen atmosphere (50 mL/min). Results are summarized in Table 1 below.

TABLE 1

|  | RM-257 (available from Merck Corporation) | LC-242 (available from BASf Corporation) | Compound of Formula 3 |
|---|---|---|---|
| Birefringence ($\Delta n$) | 0.16 | 0.15 | 0.23 |
| Temperature range of liquid crystal phase | Heating: Cr 68-73 N 124-130\| Cooling: \|125 N | Heating: Cr 63-70 N 120-125\| Cooling: \|125 N <30 Cr | Heating: Cr 56-62 N 155-162\| Cooling: \|155 N 10 Cr |

As shown in Table 1, it can be confirmed that the compound of Formula 3 according to the present invention exhibits a much higher birefringence ($\Delta n$), when compared with the conventional RM, and, from the DSC measurement value, there is liquid crystal phase behavior in a wide temperature range.

Accordingly, the RM compound according to the present invention has advantages such as solvent selectivity and secureness of process margin due to a wide temperature range of the liquid crystal phase thereof, and a high birefringence. Accordingly, the RM compound as an important material of a wide-viewing-angle liquid crystal display device of large-scale screens may be prepared into a compensation film and phase difference film and realizes an efficient thin-thickness compensation film and phase difference film. (Such wide temperature range of a liquid crystal phase allows selection of a wide range of solvents, secureness of process margin, thermostability and a high birefringence, thereby realizing a thin coating film)

The scope of the present invention is not limited to the embodiments described in the present specification and is defined only to the contents disclosed in the following claims. Those skilled in the art will appreciate that various modifications, additions and substitutions are possible, without departing from the scope and spirit of the invention as disclosed in the accompanying claims. In the following examples, the present invention will be described in more detail. It should be understand that the examples are merely to concretely explain the spirit of the invention and therefore, there is no intent to limit the invention to the examples.

What is claimed is:

1. A method of preparing a reactive mesogen compound of Formula 3, the method comprising: preparing a compound of Formula 4 below; preparing a compound of Formula 5 below from the compound of Formula 4 below; preparing a compound of Formula 6 below; preparing a compound of Formula 7 below from the compound of Formula 6 below; preparing a compound of Formula 8 below from the compound of Formula 7 below; preparing a compound of Formula 9 below by reacting the compound of Formula 5 below and a compound of Formula 8 below; preparing a compound of Formula 10 below compound from the compound of Formula 9 below; and preparing the compound of Formula 3 below from the compound of Formula 10 below:

Formula 4

Formula 5

Formula 6

Formula 7

Formula 8

Formula 9

Formula 10

Formula 3

2. The method according to claim 1, wherein the compound of Formula 5 is prepared by reacting through dropping an acryloyl chloride solution diluted in tetrahydrofuran (THF) into a mix solution of the compound of Formula 4, triethylamine (TEA) and methylene chloride (MC).

3. The method according to claim 1, wherein the compound of Formula 8 is prepared by reacting at 100° C. while stirring a mix solution of the compound of Formula 7, aminophenol (4-aminophenol), dimethylacetamide (DMAC) and ethylacetate (EAc).

* * * * *